United States Patent [19]
Kassen et al.

[11] Patent Number: 5,369,368
[45] Date of Patent: Nov. 29, 1994

[54] DEVICE FOR DETERMINING MATERIAL PARAMETERS BY MEANS OF MICROWAVE MEASUREMENTS

[75] Inventors: Rudiger Kassen, Wildbad; Albert Klein, Neunburg; Jean M. Weber, Quentin, all of Germany

[73] Assignee: Laboratorium Prof. Dr. Rudolf Berthold GmbH & Co., Wildbad, Germany

[21] Appl. No.: 42,420

[22] Filed: Apr. 2, 1993

[30] Foreign Application Priority Data

Apr. 4, 1992 [DE] Germany .............................. 4211362

[51] Int. Cl.$^5$ ............................................. G01N 22/04
[52] U.S. Cl. .................................. 324/632; 324/634; 324/636; 324/640; 324/643
[58] Field of Search ............... 324/632, 634, 636, 640, 324/639, 643

[56] References Cited

U.S. PATENT DOCUMENTS

| | | | |
|---|---|---|---|
| 3,551,806 | 12/1970 | Sasaki | 324/640 |
| 4,301,400 | 11/1981 | Paap . | |
| 4,651,085 | 3/1987 | Sakurai | 324/639 |
| 4,885,527 | 12/1989 | Lacombe | 324/636 |
| 4,890,054 | 12/1989 | Maeno | 324/640 |
| 5,144,224 | 9/1992 | Larsen | 324/639 |
| 5,194,815 | 3/1993 | Maeno | 324/632 |

FOREIGN PATENT DOCUMENTS

| | | |
|---|---|---|
| 0011185 | 10/1979 | European Pat. Off. . |
| 0372843 | 6/1990 | European Pat. Off. . |
| 2848993 | 5/1980 | Germany . |
| 3316328 | 1/1983 | Germany . |
| 3412704 | 10/1984 | Germany . |

OTHER PUBLICATIONS

Spiridonov: "Controlling The Moisture Content Of Materials . . . " Glass and Ceramics—vol. 34—(Jul.-Aug. 1977)—pp. 516-518.

*Primary Examiner*—Walter E. Snow
*Assistant Examiner*—Jose M. Solis
*Attorney, Agent, or Firm*—Spensley Horn Jubas & Lubitz

[57] ABSTRACT

A device for determining the material parameters, in particular the water content, of a substance in a dielectric medium conducted through a pipeline, the device including a waveguide of a microwave system at least partially enclosing the pipeline. Transmission or reflection of microwave radiation in the waveguide is evaluated continuously or in cycles. Continuous measurement of such media, in particular liquid media, can be effected and in particular can be made automatically without requiring steps for sample taking and performance of the measuring process per se.

13 Claims, 7 Drawing Sheets

DEVICE FOR DETERMINING MATERIAL PARAMETERS BY MEANS OF MICROWAVE MEASUREMENTS

BACKGROUND OF THE INVENTION

The present invention relates to a device for determining material parameters, such as water content, in a dielectric medium flowing through a pipeline by means of microwave measurements.

Microwave transmission or reflection measurements are a known method for determining material parameters, such as the water content, of a defined sample by means of the interaction of microwaves with this sample. In this process, the microwave radiation damping and phase shift as functions frequency are evaluated to provide a measure of the material parameter of the sample to be determined, for example.

A known option is to place the sample in a waveguide and then take transmission or reflection measurements. This method requires that discrete samples of the material to be examined be removed from time to time and placed, in a suitable form and quantity, inside a waveguide.

This method is also essentially applicable to liquid samples, but requires additional work cycles for taking a sample within defined time intervals.

OBJECT AND SUMMARY OF THE INVENTION

An object of the present invention is to improve a microwave measurement of the named type to make possible the continuous (in-line) measurement of such media, particularly of liquid media, that are guided through a pipeline.

The above and other objects are attained, in accordance with the invention by a device for determining, by means of microwave measurements, a physical characteristic of a product in a dielectric medium, in combination with a pipeline through which the medium is flowing, the pipeline having a pipeline longitudinal axis and comprising a section of at least partially dielectric material located in a measurement area, the section having a wall, an outer diameter and an interior cross section and the dielectric material having low dielectric losses, the device comprising:

a microwave transmitting/receiving system for interacting with the medium, the system including a waveguide at least partly enclosing the pipeline section to define the measuring region, the waveguide having a side wall provided with two opposed openings through which the pipeline section passes, a waveguide longitudinal axis, an internal width dimension perpendicular to the waveguide longitudinal axis, a microwave radiation input and a microwave radiation output, the measuring region being interposed between the input and the output so that radiation guided in the waveguide traverses the measuring region and has a transverse electric field which extends perpendicular to the waveguide longitudinal axis and to the width dimension, and means connected to the output for evaluating microwave radiation which has traversed the measuring region by measuring at least one of the damping and phase shift induced in the microwave radiation by product in the medium flowing through the waveguide, and wherein the pipeline section extends through the openings in the waveguide side wall in such a way that the pipeline longitudinal axis coincides with the direction of the transverse electric field formed inside the waveguide, the outer diameter of the pipeline section is not larger than the internal width dimension of the waveguide perpendicular to the pipeline longitudinal axis and perpendicular to the waveguide longitudinal axis so that the pipeline section practically completely fills the cross-section of the waveguide and the microwave radiation acts on practically all of the medium flowing through the pipeline, and the interior cross section of the pipeline section has a dimension in the direction of the waveguide longitudinal axis which decreases from the waveguide longitudinal axis to in the direction of the internal width dimension, and the mode of the transverse electric field is selected such that the intensity of the transverse electric field decreases from the waveguide longitudinal axis in the direction of the width dimension to approximately the same degree as the dimension of the pipeline section.

Extending the pipeline through the waveguide permits constant access of the measurement to the respective parameter to be determined, such as the water content of the flowing medium, and thus permits in particular the monitoring of this parameter, which in practice is often allowed to vary within predetermined limits that can also be stipulated by law for individual products.

Depending on the type of medium to be measured and the anticipated fluctuations or deviations, useful measuring intervals can then be defined within which the material parameter of interest is determined.

In this way, fully automated measurement has become possible; operating steps for taking samples and executing the measuring procedure per se are no longer necessary.

Advantageous embodiments of the device in accordance with the invention will be describe below. Preferred exemplary embodiments of the device in accordance with the invention and the individual advantages that can be achieved with them will be described in greater detail with reference to the drawings.

DESCRIPTION OF THE PREFERRED EMBODIMENTS

Figure 1A:
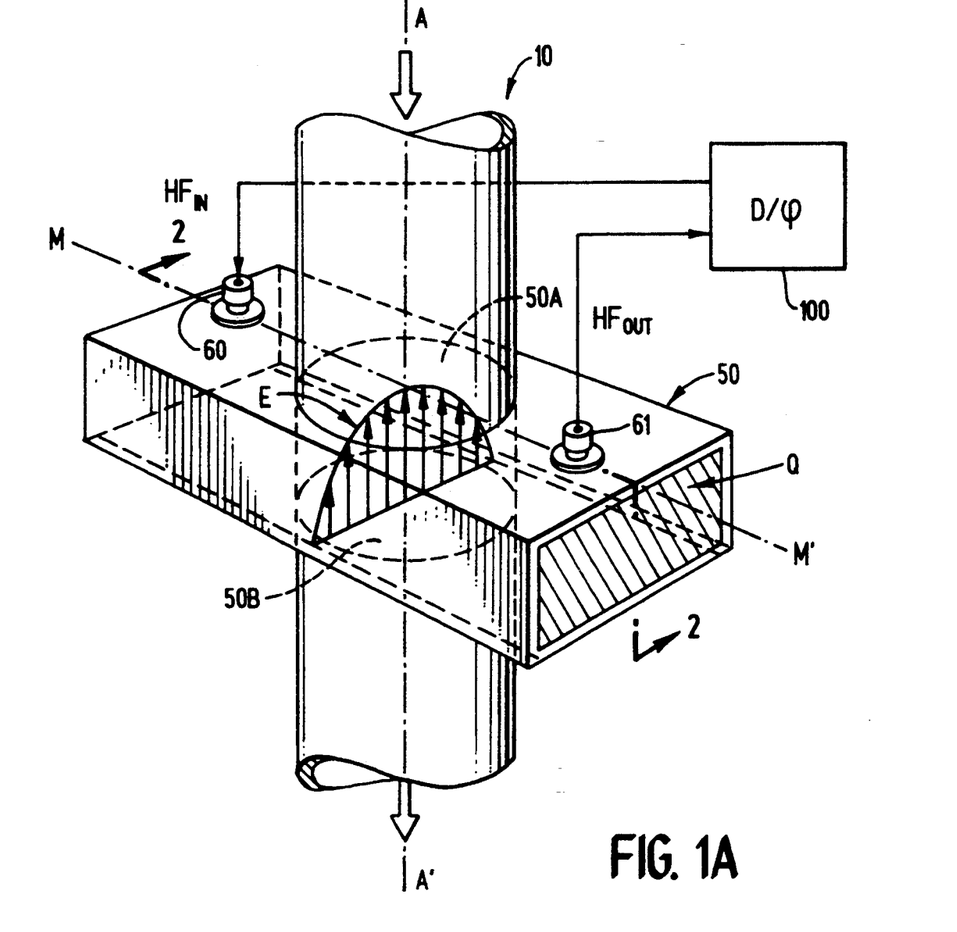
FIGS. 1A to 1D are schematic representations illustrating the operating principle of devices in accordance with the invention.

FIG. 1A shows the fundamental measuring principle: a medium flowing in a pipeline 10 (from top to bottom in the drawing) is to be evaluated with regard to its water content. For this purpose a waveguide 50 with a rectangular cross-section Q is used that has openings 50A, 50B at its upper and lower ends, respectively, through which the pipeline 10 passes. On both sides of the pipeline 10, microwaves are coupled in and out of waveguide 50 via schematically represented input and output connections 60, 61 in such a way that these microwaves necessarily pass through the pipeline as well as through the medium to be measured that is flowing inside it, thus influencing the measurable properties of the microwave (damping and/or phase) in a way that can be evaluated.

For this purpose, the pipeline 10 is made of a nonconductive, dielectrical material. The longitudinal axis A—A' of the pipeline 10 extends perpendicularly to the longitudinal axis M—M' of the waveguide 50 such that the schematically represented transverse electric field E of the magnetic $H_{10}$ wave extends parallel to the axis A—A' of the pipeline 10, as shown by the parallel arrows in FIG. 1A, whose points end at a half sine wave that corresponds to the field extension of the electrical field that is present there. As a result, the maximum intensity of the electrical field is found at the point where the wave must pass through the diameter of the pipeline 10, i.e., where the largest damping D is consequently to be anticipated. Through comparison of the sine path of the field intensity E with the cross-sectional circular surface of the pipeline 10 perpendicular to it, it can be easily seen that an approximately comparable reduction in the thickness of the layer of medium to be radiated, i.e. in the direction of waveguide axis M—M', is mirrored by the drop of the electrical field intensity E toward the edges of the waveguide 50, so that an at least approximate compensation occurs in the sense that the "available" field intensity is approximately proportional to the damping to be anticipated. This advantageously affects the measurement sensitivity and measurement precision, with the result that the pipeline 10 used should fill the cross-section Q of the employed waveguide 50 as fully as possible, which can be normally achieved with a pipeline diameter that as a rule is preset by selecting a microwave measuring frequency that results in a corresponding cross-section Q.

With this measurement arrangement, represented schematically in FIG. 1A, it is possible to feed in microwaves, for instance, at the input 60 ($HF_{in}$) that are then again decoupled at the output 61 ($HF_{out}$) after having radiated through the medium. The desired conclusions about the water content of the medium flowing through the pipeline 10 can be reached by performing a generally known measurement in an evaluation unit 100, which essentially comprises a measurement of the damping, or attenuation, D and/or the phase $\phi$.

Figure 1B:
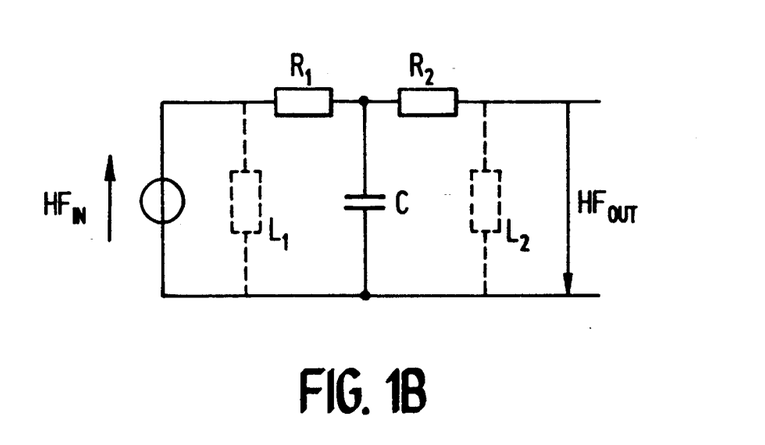

FIG. 1B shows a simple equivalent circuit diagram of the principal arrangement shown in perspective in FIG. 1A; the particular point of interest is that the two openings 50A, 50B in the opposite side walls of the waveguide 50 with the pipeline 10 penetrating it lead to interferences in the incident microwaves that are approximately represented in the equivalent circuit diagram of FIG. 1B by a capacitance C that leads to an impedance mismatch.

Figure 1C:
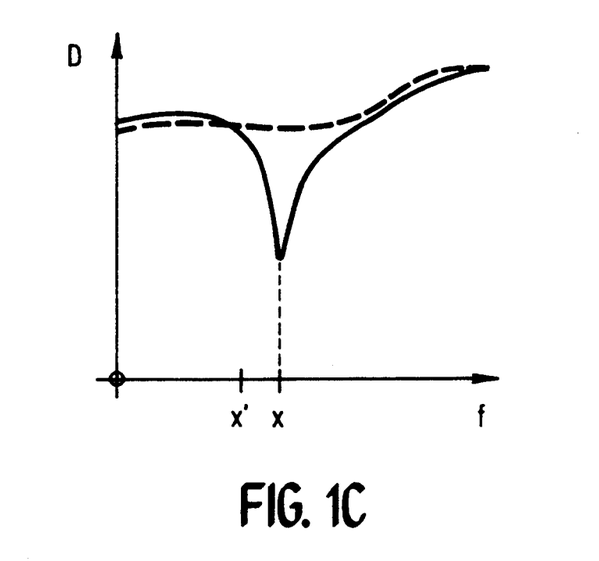
Figure 1D:
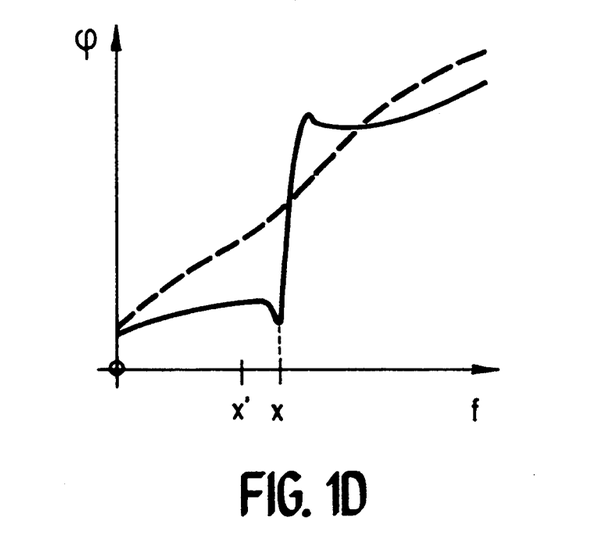

If an arrangement having the form shown in FIG. 1A in accordance with the equivalent circuit diagram 1B is used to measure (FIGS. 1C, 1D) damping D and phase $\phi$ (first empty, i.e. without a medium flowing through it), the curves shown in solid line in FIGS. 1C and 1D result, i.e. at the resonance frequency x, a sharp break occurs during in the damping curve and a correspondingly sharp jump occurs in the curve of the phase $\phi$. When the pipeline 10 is filled with a medium other than air, the resonance frequency is displaced to correspond to the lower value x'.

Because the damping, or attenuation, and the phase curves of, for instance, a transmission measurement are evaluated as a function of the microwave frequency (evaluation unit 100) during determination of the material properties of the material, it is therefore particularly important that, during these measurements, the curves of these two measurement values as a function of the frequency be as smooth as possible (in the ideal case, a linear shape).

It is already possible to take measurements with the measuring arrangement represented schematically in FIG. 1A; however, the resonance effects that are due to the capacitance C lead to quantitatively unsatisfactory measurement results. An essential improvement can be attained by means of the measures described below; with their use the function curves assume the forms shown in broken lines in FIGS. 1C and 1D, i.e. with their use an approximately linear or at least smooth shape can be attained for these curves that are essential for the evaluation.

Figure 2:
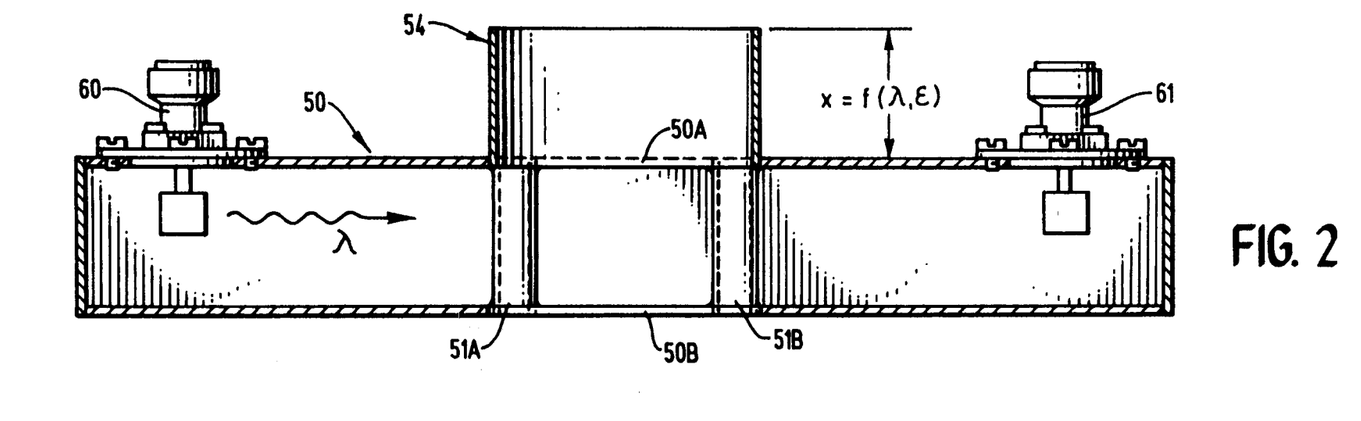
FIG. 2 is a longitudinal section in the plane M—M' of FIG. 1 through an exemplary embodiment of a waveguide.
Figure 3:
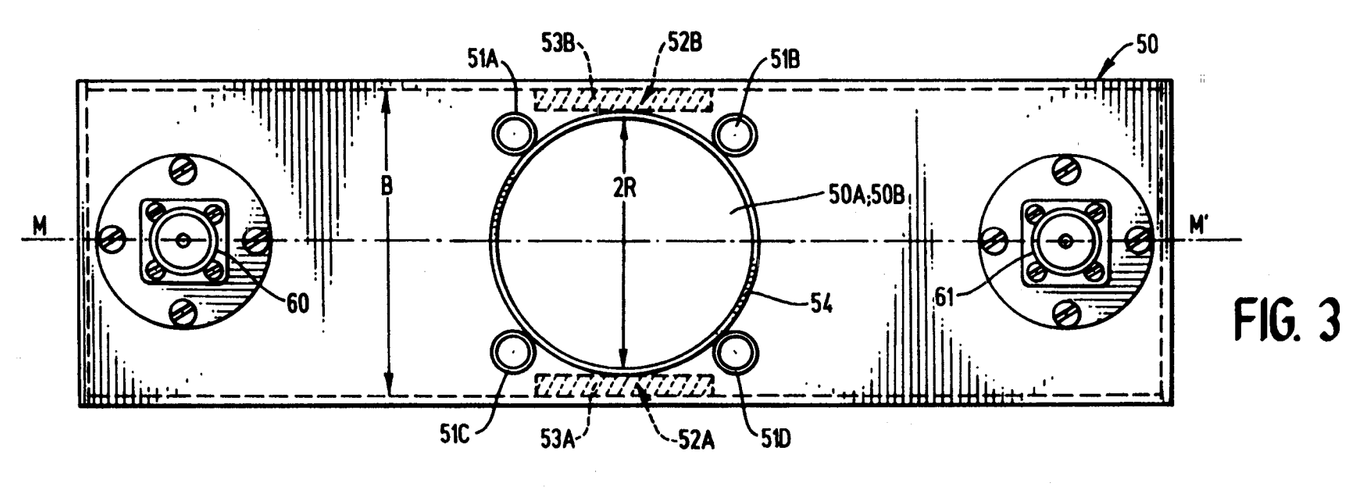
FIG. 3 is a top plan view of the waveguide in accordance with FIG. 2.
Figure 4:
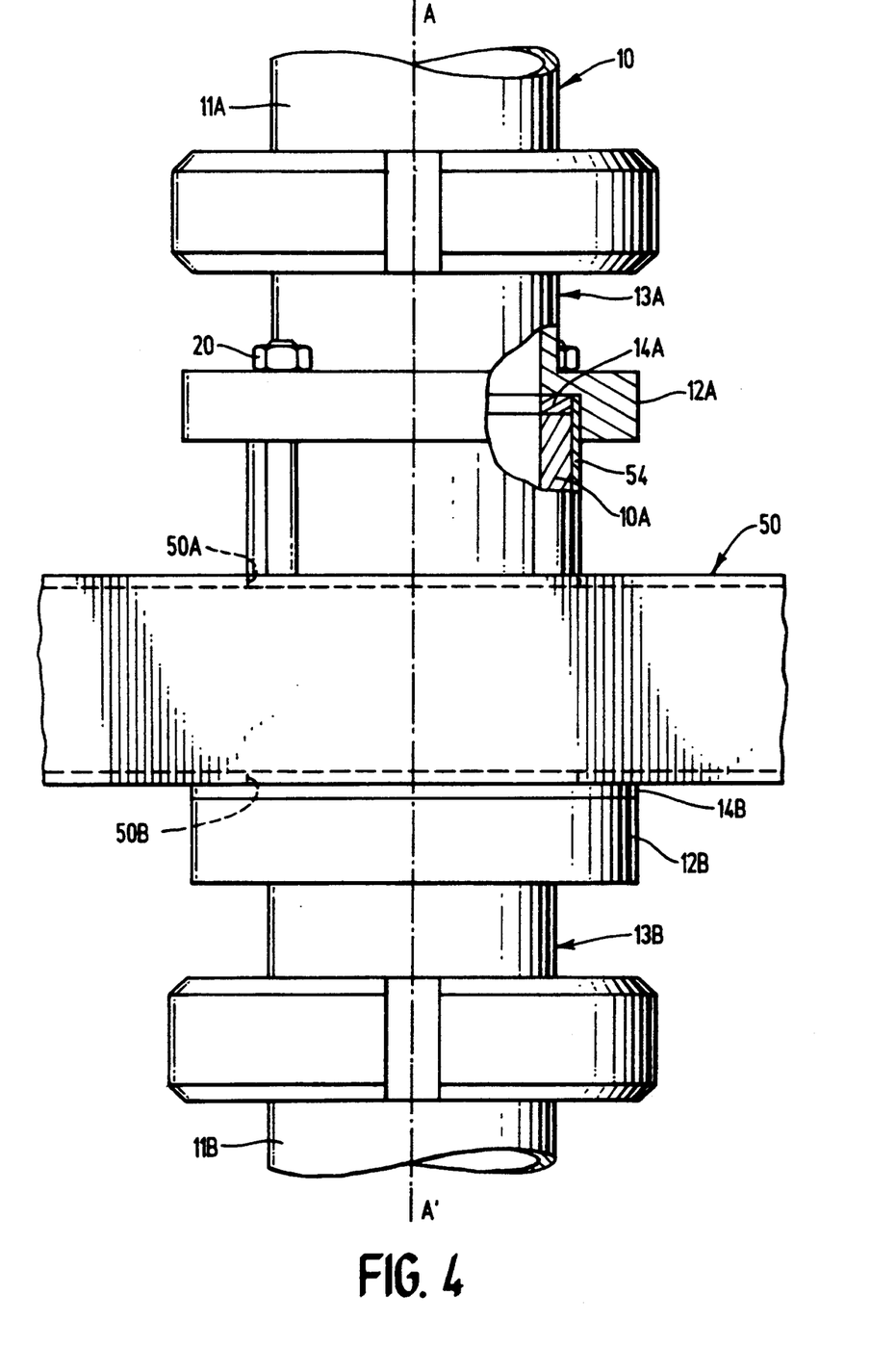
FIG. 4 is a partly cut-out side view of a practical application of the waveguide of FIGS. 2 and 3 with a pipeline.

FIGS. 2 through 4 illustrate these, and further, measures for increasing the measuring sensitivity and for improving the measuring precision. The fundamental idea for improving the measurement operation first lies in compensating the effects of the capacitance C (equivalent circuit diagram of FIG. 1B) as extensively as possible by arranging inductances L1/L2, which are likewise shown in broken lines in the equivalent circuit diagram of FIG. 1B corresponding to the smoothing of the function curves they effect in FIGS. 1C and 1D.

It has been shown that, structurally, this type of inductance is possible, represented in the exemplary embodiment by connecting bars 51A, B, C and D, which are disposed near the walls of the pipeline 10 as well as near the walls of the waveguide 50, extend parallel to the pipeline 10, and extend from the top wide side wall of the waveguide 50 down to the bottom wide side wall thereof. The "inductive effect" of such components is capable of at least substantially compensating the effect of the pipeline 50 guided through the openings 50A, 50B that basically adulterates the measurement so that the flowing medium can be measured cleanly, so to speak, with the microwave arrangement.

The connecting bars 51A–51D are suitably disposed symmetrically, the shaping and number of these bars can be selected within specific limits, are dependent on the dimensioning of the waveguide in an actual application, and can be empirically ascertained for an actual individual cases.

It can be recognized from the top plan view of FIG. 3 that, as opposed to the sought optimum, the diameter 2R of the openings 50A/50B (corresponding to the outer diameter of the pipeline 10) is slightly smaller than the interior width B of the wide transverse dimension of waveguide 50 extending in the same direction; this can be based on the fact that with a preset diameter 2R, the microwave transmitting frequency (because of legal stipulations, for instance) cannot be selected precisely such that the ideal condition B=2R is met. In this case it is useful to damp the two gaps 52A and 52B formed between the pipe wall and the parallel side walls at the narrow sides of the waveguide by means of suitable layers 53A and 53B of radiation absorbing material in order to exclude the field components occurring there from the measurement, because in the end they would lead to measuring a mixed dielectric, thus decreasing the measurement sensitivity.

FIG. 4 shows a detailed representation of structural embodiment of a pipeline 10 extended through waveguide 50. The part of the pipeline 10 leading through the waveguide 50 is formed by a partial element 10A, which is transparent to electromagnetic waves, wherein the transition from the metallic, typically used connecting lines 11A, 11B to this partial element 10A, for instance can be constituted by structures used in the food industry ("viewing lanterns"), with which a glass or ceramic pipe can make a transition between the metallic pipeline sections 11A, 11B as partial element 10A with the aid of two metal flanges 13A and 13B. For this purpose flanges 12A and 12B, in particular, are provided, each flange having an whose inner groove in which a respective axial end of partial element 10A is seated, and inserted seals 14A, 14B are provided as a seal against water in the pipeline as well as against the waveguide measuring system. The lower flange 12B resting against the waveguide 50 is sealed with a seal 14B of soft tin; the upper flange 12A, which rests against the partial element 10A, is provided with an additional groove, where a conventional sealing ring 14A is inserted.

The bolts 20 needed to brace the flange are guided through sleeves that are in turn guided through the waveguide 50, preferably through the "equivalent inductances", i.e. the bars 51A . . . 51D. These sleeves are tightly welded at their entry positions on the top and bottom of the waveguide.

As a further feature improves the quality of the microwave measurement, a cylindrical, metallic cap 54 that tightly encloses the wall of the partial element 10A of the pipeline 10 is attached coaxially to one, or each, of openings 50A, 50B of the waveguide 50. This pipe cap 54 essentially performs two functions: it prevents, on the one hand, electromagnetic waves from exiting the waveguide 50 and being radiated into the surrounding area; and, on the other hand, it prevents electromagnetic waves that could distort the measurement results from being coupled into the waveguide 50.

This can be based on the longitudinal flows induced by the microwaves in the waveguide reaching the decoupling point on the opposite side via the metallic wall of the waveguide. In doing this, the character of the microwave is retained as a waveguide wave that is guided in the direction of the line, even when the microwave passes through the medium to be measured. This contributes to the improvement of the crossover behavior of the microwave arrangement in the same way as the "equivalent inductances" described above. The longitudinal flows, which flow over the cylindrical cap 54, can likewise incite a waveguide wave of type $H_{11}$ in the pipeline itself; this is, however, of secondary significance for measurement.

The arrangement of such cylindrical caps as the cylindrical cap 54 must be effected such that disturbing reflections at the transition to the partial element 10A have no retrograde effects on the field distribution inside the waveguide. Basically the field components that penetrate the non-conductive pipe are reflected at the metallic flanges and, because of the low damping of the non-conductive pipe, steps must be taken that these field components reflected by the lower and upper flanges are superimposed in antiphase, so that they cancel each other out and no longer prove detrimental to the field distribution inside the waveguide.

This is assured by providing only one cap 54 having a length X as a function of n and $\lambda_\epsilon$ selected according to the equation:

$$X = \frac{2n+1}{4} \lambda_\epsilon,$$

where n=0, 1, 2, . . .

$\epsilon$=dielectric constant associated with the cylindrical cap and $\lambda_\epsilon$=microwave wavelength in the region of the cylindrical cap.

This "canceling out condition" assures the desired effect.

Essentially, this can also be achieved by a respective cylindrical cap at each of the two opposite openings in the wide side walls of waveguide 50, which then must have different lengths. The solution represented in the exemplary embodiment, a single cylindrical cap 54 disposed on one side, has been shown to be structurally the simplest.

Suitably, the length of the partial element 10A and the length of the cylindrical cap 54 are matched to each other such that the cap 54 in the annular groove of the flange 12A rises above the partial element 10A by the thickness of the sealing insert 14A, so that a good high-frequency seal is attained.

Figure 5:
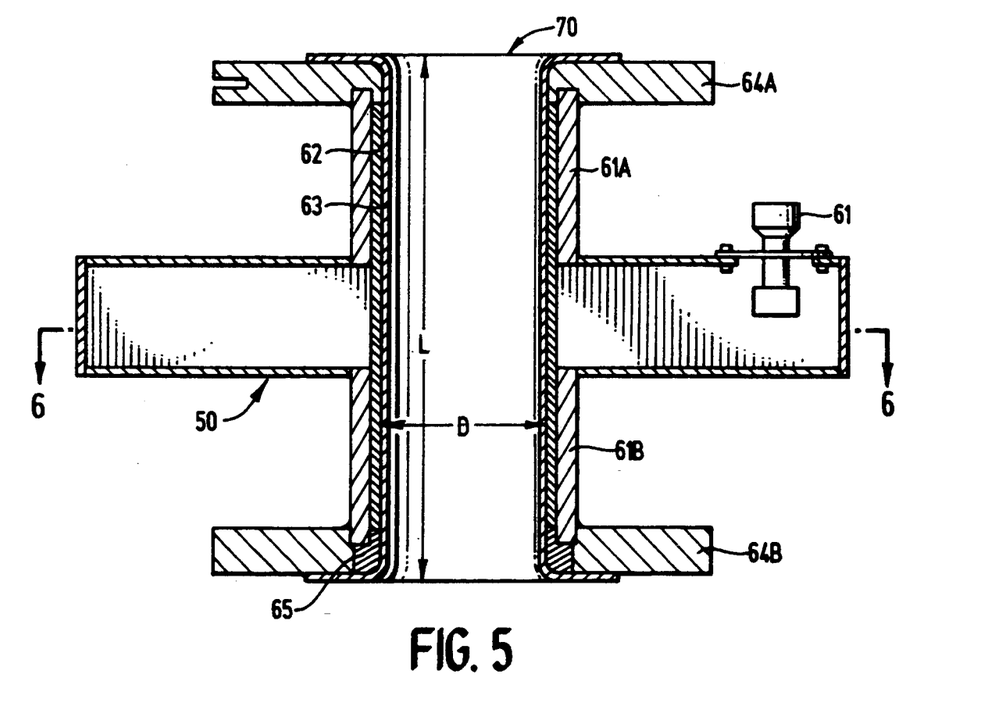
FIG. 5 is a vertical section of a further exemplary embodiment of a waveguide having an integrated pipeline section.
Figure 6:
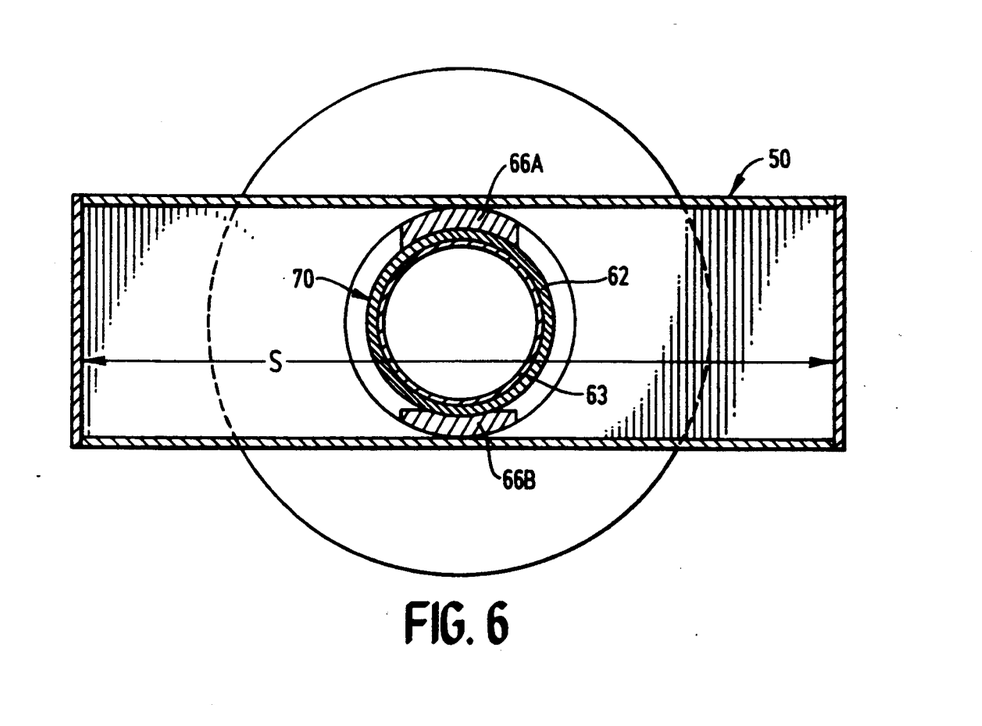
FIG. 6 is a horizontal section in the plane V—V' of FIG. 5.

FIGS. 5 and 6 show a second exemplary embodiment of a pipeline section with an integrated waveguide:

The pipeline section 70 comprises in its outer construction two front-face flanges 64A, 64B and two cylindrical, metallic outer pipes 61A, 61B, whose one end terminates in the flanges 64A, 64B, and whose other end is fixed in the opposite openings of the waveguide 50 so that the longitudinal plane of the waveguide 50 comes to rest perpendicularly to the longitudinal axis of the pipeline section 70.

Towards the interior, the flanges 64A, 64B overlap a continuous inner ceramic pipe 62. The inside of the ceramic pipe 62 and the adjoining outer areas and front areas of the flanges 64A, 64B are lined with a tube 63 of PTFE (Teflon ®) that serves to seal the described structure against the medium to be measured as it flows through.

It can be seen from the cross-sectional representation of FIG. 6 that the outer diameter of the metallic outer pipes 61A, 61B corresponds to the width of the waveguide 50, so that in the area in which the ceramic pipe 62 extends through the waveguide 50, a space or gap remains at the edges between the outer wall of the ceramic pipe 62 and the opposite inner wall of the waveguide 50.

In this exemplary embodiment (see also the cross-sectional representation of FIG. 3) this space is filled by components acting as inductances that are intended to compensate for the influence of the capacitance caused by the two openings of the waveguide, as explained above in more detail.

These components are embodied here as metallic, arcuate screening elements 66A, 66B that are dimensioned such that they cause differing phase shifts in the microwave radiation passing through them; this can be attained by means of a differing cross-sectional structuring of the two elements 66A, 66B, for example, as shown in FIG. 6 where elements 66A and 66B have respectively different cross sections.

The intent of this measure is as follows: with a medium that has a high damping, a significant amount of microwave radiation passes the pipeline 70 from input to the output. These microwaves thus represent an undesirable radiation leakage. With the arrangement of the screening elements 66A, 66B, which are embodied asymmetrically in the aforementioned sense, it is at least partially possible that the path difference between both microwave parts is nearly $\lambda/2$, so that a canceling-out effect is attained when these two microwave components overlap in the receiving area of the waveguide 50, that this undesirable radiation leakage can be eliminated, at least to a great extent. The useful dynamic range of the device is increased substantially by this, so that even a medium with very high damping can be measured with sufficient dynamics.

Figure 8:
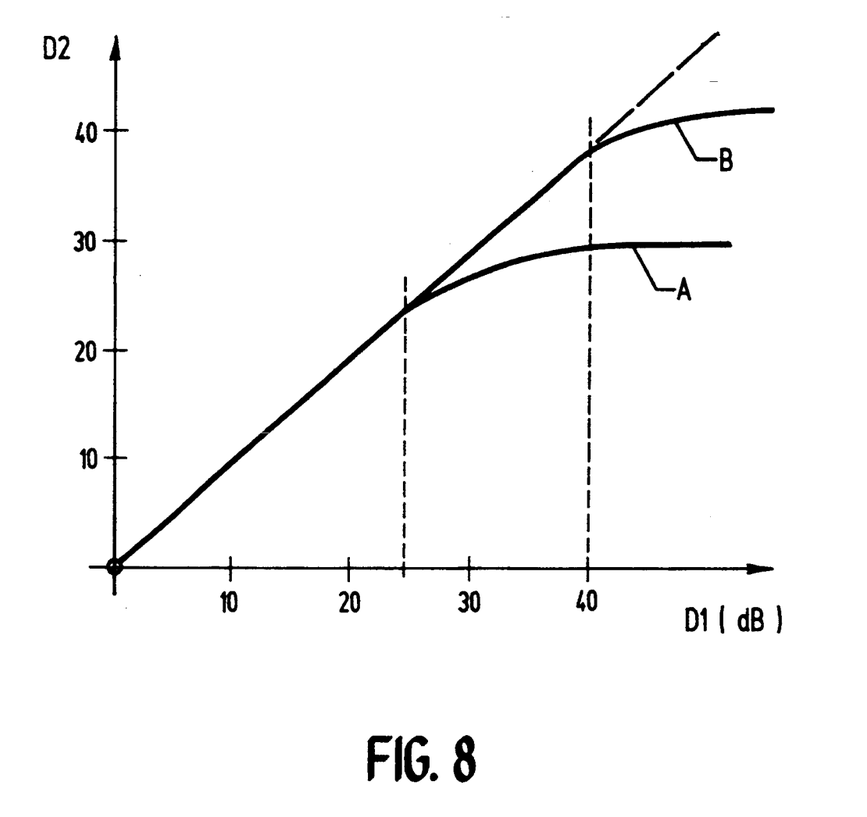

FIG. 8 schematically shows this improved behavior of the device in accordance with the invention. The two curves A or B represented show relation between the actual damping D1 of a substance to be measured and the damping D2 detected and displayed by the measuring device. A precise measurement in this representation means that the function D2=f(D1) is as linear as possible.

With symmetrical screening elements (see FIG. 3) this was the case in practical experiments with an embodiment of the device up to a damping of approximately 25 Db (curve A).

With higher damping, such as can occur, for example, with a substance to be measured that has a high electrolyte conductivity because of a high salt content, lower damping D2 is detected and displayed than the one corresponding to the actual damping D1 of the substance to be measured because of the aforementioned radiation leakage that during increasing damping of the substance to be measured has an increasing influence on the total result as a sum of transmitted radiation and radiation leakage.

When asymmetrical screening elements 66A, 66B (FIG. 6) are used, the mutual cancellation effect of the two components of the radiation leakage reduces the influence of the radiation leakage in relation to the transmitted radiation as a "useful radiation" so that as a result it was possible to expand the area of linearity (curve B); in other words, a precise measurement could even be taken with very high damping over a range of approximately 40 Db.

In the aforementioned, practical exemplary embodiment of the device in accordance with the invention, shown in FIGS. 5 and 6, the length L of the pipeline section 70 was 172 mm, the inner diameter D of the ceramic pipe 62 was 44 mm and the length S of the waveguide 50 was 256 mm. Measurements were taken in a microwave frequency range of 2.7 to 3.4 Ghz, the substance measured was cream cheese, and its dry mass content was determined. An apparatus marketed by Laboratorium Prof. Dr. Rudolf Berthold GmbH & Co. KG, Wildbad, Germany under the trade name "Berthold MicroMoist" served as the evaluation unit 100 (FIG. 1).

Figure 7:
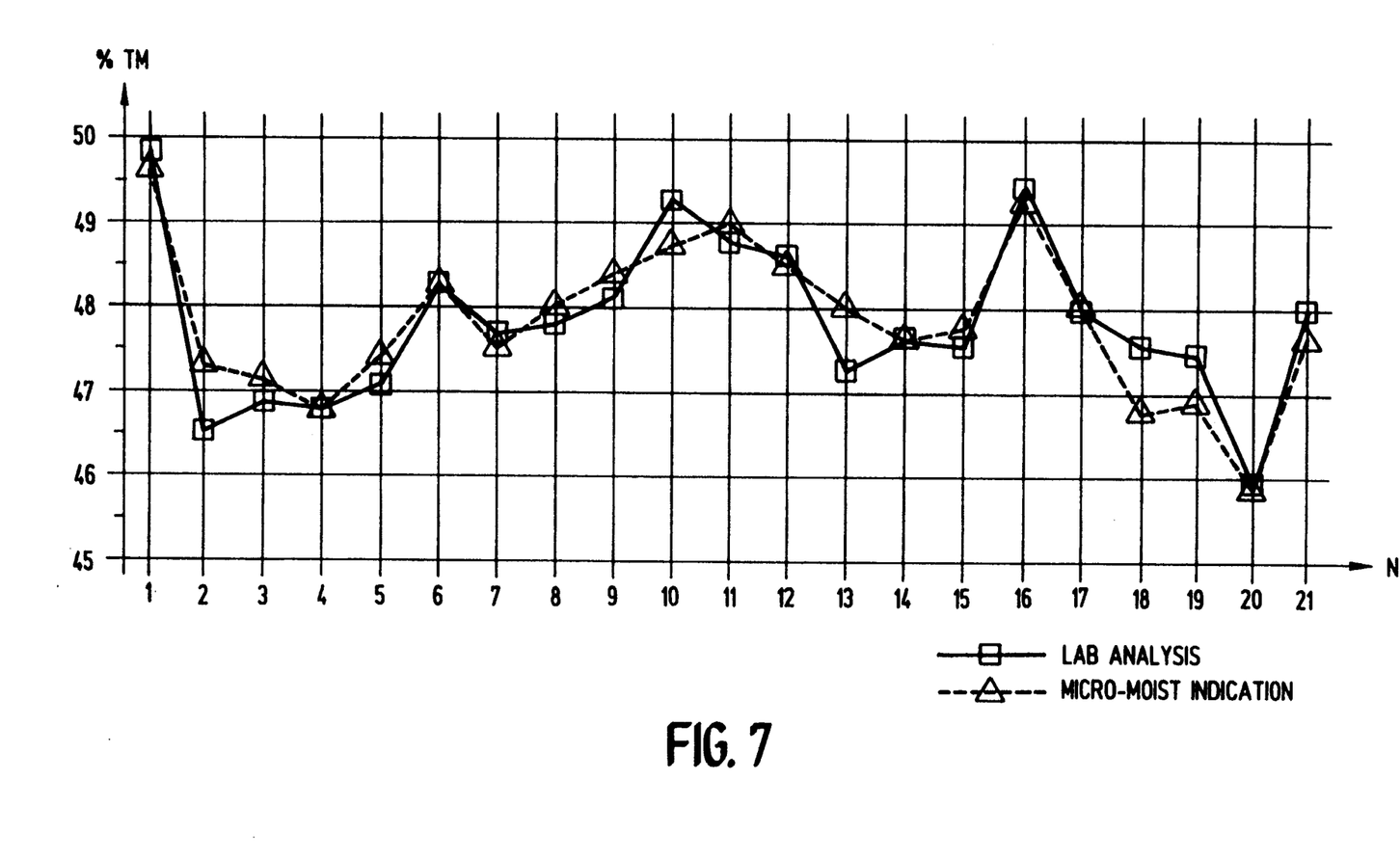
FIGS. 7 and 8 are each a schematic representation of measurement results.

The measurement values obtained in this way are shown in FIG. 7: %-TM stands for the dry mass content in percent of the cream cheese, and N are the measurement points (21 measurement points in the example). The measurement points, designated by triangles, were obtained with the device in accordance with the invention described above; the measurement points designated by squares were taken from a lab analysis as a control. The measurement points to be compared show a standard deviation of only ±0.37%-TM from the lab values.

With the described arrangement, a rectangular waveguide was used; one of the flanges (64B) was equipped with an inner threaded ring 65 for holding the ceramic pipe 62 in the flange 64B. It is basically just as feasible, however, to use a round waveguide, wherein the magnetic ground wave that penetrates the medium is the $H_{11}$ wave.

This application relates to subject matter disclosed in German Application number P 42 11 362.8-52, filed on Apr. 4, 1992, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A device for determining, by means of microwave measurements, a physical characteristic of a product in a dielectric medium, in combination with a pipeline through which the medium is flowing, said pipeline having a pipeline longitudinal axis and comprising a section composed at least partially of dielectric material located in a measurement area, said section having a wall, an outer diameter and an interior cross section and the dielectric material having low dielectric losses, said device comprising:

a microwave transmitting/receiving system for interacting with the medium, said system including a waveguide at least partly enclosing the pipeline section to define the measuring region, said waveguide having a side wall provided with two opposed openings through which said pipeline section passes, a waveguide longitudinal axis, an internal width dimension perpendicular to said waveguide longitudinal axis, a microwave radiation input and a microwave radiation output, said measuring region being interposed between said input and said output so that radiation guided in said waveguide traverses said measuring region and has a transverse electric field which extends perpendicular to said waveguide longitudinal axis and to said width dimension, and means connected to said output for evaluating microwave radiation which has traversed said measuring region by measuring at least one of the damping and phase shift induced in the microwave radiation by product in the medium flowing through said waveguide, and wherein said pipeline section extends through said openings in said waveguide side wall in such a way that said pipeline longitudinal axis coincides with the direction of said transverse electric field formed inside said waveguide, the outer diameter of said pipeline section is not larger than said internal width dimension of said waveguide perpendicular to said pipeline longitudinal axis and perpendicular to said waveguide longitudinal axis so that said pipeline section substantially completely fills the cross-section of said waveguide and the microwave radiation acts on substantially all of the medium flowing through said pipeline, and the interior cross section of said pipeline section has a dimension in the direction of said waveguide longitudinal axis which decreases from said waveguide longitudinal axis in the direction of said internal width dimension, and the mode of the transverse electric field is selected such that the intensity of the transverse electric field decreases from said waveguide longitudinal axis in the direction of said width dimension to approximately the same degree as said dimension of said pipeline section.

2. The device as defined in claim 1 wherein said waveguide is a rectangular waveguide.

3. The device as defined in claim 1 wherein said openings in said waveguide side wall create a capacitance, and said device further comprises means forming inductances in the vicinity of said openings for at least approximately compensating for the capacitance.

4. The device as defined in claim 3 wherein said means forming inductances comprise conductive connecting bars between opposed portions of said side wall of said waveguide and extending parallel to said pipeline longitudinal axis.

5. The device as defined in claim 4 wherein there are least two of said connecting bars in close proximity to said wall of said pipeline section and to said side wall of said waveguide.

6. The device as defined in claim 5 wherein there is a gap between said wall of said pipeline section and said side wall of said waveguide, and said device further comprises a layer of a radiation absorbing material disposed in said gap.

7. The device as defined in claim 4 further comprising connecting elements extending through said connecting bars for connecting said waveguide and said pipeline section together.

8. The device as defined in claim 3 wherein said means forming inductances are constituted by two metal screen elements each disposed adjacent a respective diametrically opposed portion of said pipeline section, said metal screen elements additionally functioning as an asymmetrical screen which cause microwaves passing around one side of said pipeline section to said output are at least partially canceled out by microwaves passing around the other side of said pipeline section to said output.

9. The device as defined by claim 8 wherein said metallic screen elements rest against said pipeline and that, to attain asymmetry, said metal screen elements have respectively different cross sections.

10. The device as defined in claim 1 wherein said pipeline section comprises: an element having an outer cross section and made at least partially of a dielectric material exhibiting low dielectric losses with respect to the microwave radiation; and two cylindrical caps each having a diameter at least essentially equal to the diameter of the outer cross section of said element, each of said caps being seated coaxially in a respective one of the openings of said waveguide so that said caps form a cross with said waveguide to at least substantially completely screen said element so that microwave radiation which enters said pipeline section is guided in said pipeline section.

11. The device as defined in claim 10 wherein said cylindrical caps are of unequal lengths, so that electrical irregularities in said pipeline are compensated to a substantial extent in the region of said waveguide thus minimizing the disturbing effect of such irregularities on the measurement.

12. The device as defined in claim 1 wherein said pipeline section comprises: an element having an outer cross section and made at least partially of a dielectric material exhibiting low dielectric losses with respect to the microwave radiation; and a cylindrical cap whose diameter is at least essentially equal to the diameter of the outer cross section of said element, said cap being seated coaxially in one of the openings of said waveguide so that said cap forms a T-shaped structure with said waveguide to at least nearly completely screen said element so that microwave radiation which enters said pipeline section is guided in said pipeline section.

13. The device as defined in claim 1 further comprising means forming watertight connections between said pipeline and said waveguide.

* * * * *